United States Patent [19]

Nakamichi et al.

[11] Patent Number: 5,700,410
[45] Date of Patent: Dec. 23, 1997

[54] METHOD OF MANUFACTURING WAX MATRICES

[75] Inventors: Kouichi Nakamichi, Koga-gun; Shougo Izumi, Kameoka; Hiroyuki Yasuura, Kusatsu, all of Japan

[73] Assignee: Nippon Shinyaku Co., Ltd., Japan

[21] Appl. No.: 416,816

[22] PCT Filed: Oct. 14, 1993

[86] PCT No.: PCT/JP93/01472

§ 371 Date: Jun. 7, 1995

§ 102(e) Date: Jun. 7, 1995

[87] PCT Pub. No.: WO94/08568

PCT Pub. Date: Apr. 28, 1994

[30] Foreign Application Priority Data

Oct. 16, 1992 [JP] Japan .................. HEI-4-304986

[51] Int. Cl.⁶ .................. A61K 9/26; B29B 7/46
[52] U.S. Cl. .............. 264/122; 264/211.11; 264/211.23; 264/349
[58] Field of Search .......... 264/177.11, 211.11, 264/211.23, 4, 349, 109, 122; 425/204

[56] References Cited

U.S. PATENT DOCUMENTS

| | | | |
|---|---|---|---|
| 2,245,640 | 6/1941 | Beattie | 264/211.11 |
| 3,487,138 | 12/1969 | Hess et al. | 264/122 |
| 4,132,753 | 1/1979 | Blichare et al. | 264/122 |
| 4,849,141 | 7/1989 | Fujioka et al. | 264/211.11 |
| 4,957,681 | 9/1990 | Klimesch et al. | 264/211.23 |
| 5,151,026 | 9/1992 | Andersen et al. | 264/349 |
| 5,183,690 | 2/1993 | Carr et al. | 264/211.11 |
| 5,456,923 | 10/1995 | Nakamichi et al. | 424/489 |
| 5,543,099 | 8/1996 | Zhang et al. | 264/122 |

FOREIGN PATENT DOCUMENTS

| | | |
|---|---|---|
| A 57224/86 | 11/1986 | Australia . |
| 0 204 596 | 12/1986 | European Pat. Off. . |
| 368247 | 5/1990 | European Pat. Off. . |
| 0 529 396 A1 | 3/1993 | European Pat. Off. . |
| 0 580 860 A1 | 2/1994 | European Pat. Off. . |
| 2 273 512 | 1/1976 | France . |
| 2 273 584 | 1/1976 | France . |
| 24 39 538 | 3/1976 | Germany . |
| 2-223533 | 9/1990 | Japan . |
| 1 513 166 | 6/1978 | United Kingdom . |

OTHER PUBLICATIONS

English language abstract of FR 2273512 from Item 1 from file: 350: Derwent World Pat.
English language abstract of DE 2439538 from Item 1 from file: 350: Derwent World Pat.
English abstract of EP 529396 from Item 1 from file: 351: Derwent WPI.
Journal of Pharmaceutical Sciences, Vo. 62, No. 1 (Jan. 1973), F.W. Goodhart, et al "Design and use of a Laboratory Extruder for Pharmaceutical Granualrions", pp. 133–136 lines 41–44.

*Primary Examiner*—Mathieu D. Vargot
*Attorney, Agent, or Firm*—Graham & James LLP

[57] ABSTRACT

A method of producing a wax matrix for controlled release of a pharmaceutically active ingredient is provided. The method includes the steps of feeding a wax and a pharmaceutically active ingredient into a multi-screw extruder and thoroughly mixing the wax with the pharmaceutically active ingredient using the multi-screw extruder to form a wax matrix. The wax matrix thus produced provides a controlled release of the active ingredient.

15 Claims, 2 Drawing Sheets

METHOD OF MANUFACTURING WAX MATRICES

TECHNICAL FIELD

This invention relates to a method of producing a wax matrix.

The term 'wax matrix' is used herein to mean a device chiefly associated with the controlled release or masking of a drug in the form of an active ingredient entrapped in a wax lattice.

The term 'extruder' is used herein to mean a screw kneader-extruder which is in broad use chiefly in the processing of foodstuffs (cereals, protein, animal meat, fish meat, etc.) in food industry.

BACKGROUND ART

The conventional technology for the production of a wax matrix includes a fusion method, a spray method, a fusion-spray method, and so on.

Among them, the fusion-spray method is a technique under intensive research these days for the production of wax matrices. The fusion-spray method is a method for producing a wax matrix using a fluidized bed granulator, tumbling fluided bed granulator or other machine, which comprises either spraying a wax melted at a temperature over its melting point against crystals of an active ingredient, a powdery composition containing the active ingredient or a granulated version thereof or spraying a hot molten mixture of a wax and a powder (a crystalline active ingredient and a powdery excipient) in a cold atmosphere. Therefore, the fusion-spray method is not only free from the problems associated with the melting method [e.g. poor content uniformity and limiting concentration of carrier (wax) and powder (crystals and excipient particles)] but also free from the drawbacks of the spray method (residues of the organic solvent, measures for the disposal of waste gas and water, operator health management, etc.).

However, the fusion-spray method also has certain disadvantages, one of which is concerned with yields. Thus, since the wall structure of the granulator used in the fusion-spray method is made for the most part of metal, the load tends to stick to the internal wall which is of high heat conductivity. Moreover, the formation of secondary and tertiary particles due to coagulation of primary particles tends to occur in this method so that in order to insure a constant release rate of the active ingredient, it is generally mandatory to sieve off the secondary and tertiary particles following granulation.

Moreover, in the fusion-spray method in which a molten wax is sprayed, the wax must be consistently maintained at temperatures not below the melting point of the wax lest the melt will be readily solidified in the transport line and spray nozzle. Furthermore, excessive heating would result in a degradation of the active ingredient beyond the tolerable limit.

Furthermore, since the fusion-spray method is a batch method just as the other conventional methods, disadvantages are inevitable in mass production. Thus, in order that a large amount of wax matrix may be produced batch-wise in a given time period, large-scale equipment is required but the larger the equipment, the greater is the difficulty in setting production parameters and the production time is prolonged. Moreover, any batch method involves the problem of batch-to-batch variation in quality.

DISCLOSURE OF INVENTION

This invention has for its object to provide a method of producing a wax matrix free from the disadvantages of the prior art technology.

The inventors of this invention found that the above object can be successfully accomplished by utilizing an extruder which is capable of processing a substrate material in a continuous sequence and have arrived at this invention.

There is substantially no technology utilizing an extruder in the pharmaceutical field. Probably all that is known is the patent application filed by the present applicant, which discloses a method for producing a solid dispersion by means of an extruder (PCT/JP92/00470).

At this junction, the mechanism of the main part (load processing part) of the extruder is briefly described. Generally the main part of an extruder comprises a cylindrical structure called 'barrel', a die which corresponds to a delivery port, and a screw. The barrel usually comprises a plurality of unit barrels and the screw extends through them. The screw is available in various geometries, viz. trapezoidal screw, trapezoidal cut screw, trapezoidal reverse cut screw, ball screw, kneading paddle, etc., which can be used in any desired combination. The load fed to the extruder is forced to advance, shorn and mixed by the screw within the barrel structure and extruded from the orifice or orifices of the die. Usually, the temperature of each unit barrel and that of the die can be independently controlled.

The extruder is available in two types, namely a single-screw extruder having one screw and a multi-screw extruder having two or more screws. In the practice of this invention, a multi-screw extruder is preferably employed. The multi-screw machine in which the plural screws interferring with each other do not entrain the active ingredient and, moreover, the intermeshing of the screws provides a high energy output. In this invention, the use of a twin-screw extruder, among multi-screw extruders, is sufficient to achieve the above-mentioned object.

The present invention is hereinafter described in detail.

The gist of this invention resides in the use of a multi-screw extruder (hereinafter referred to generally as an extruder) in the production of a wax matrix.

In practicing this invention, an extruder which is in routine use by the food industry in the main can be used as it is.

As an embodiment of this invention, there can be mentioned a method for producing a wax matrix which comprises mixing an appropriate wax with an active ingredient physically in powdery state, feeding the resulting mixture to an extruder set to barrel and die temperatures below the melting point of said wax, and operating the extruder.

The technology for physical mixing of a wax with an active ingredient includes the technology employing a kneader-mixer, twin shells mixer, double cone mixer, cubic mixer, ribbon mixer or the like.

Feeding of the wax-active ingredient mixture into the barrel structure of an extruder can be carried out by means of a feeder with which the extruder is generally provided but any other device adapted to feed a particulate load at a constant rate can be used for feeding said mixture into the extruder barrel structure. Among such feeding devices may be reckoned a screw feeder, a table feeder, a belt-conveyerized quantitative feeder, an electromagentic feeder, and so on.

The number of revolutions (processing speed) of the screw or screw assembly can be set within the allowable limits of the extruder used. Generally speaking, the greater the overall length of the barrel structure of the extruder, the higher is the maximum permissible rotational speed of the screw.

The screw geometry and combination of unit screws can be more or less freely selected. It is preferable to employ at least one paddle which is generally called 'kneading paddle' which delivers high kneading and shearing forces.

The orifice configuration of the extrusion die is not particularly restricted and includes circular, elliptical, square, hexagonal, and various other configurations. Where the orifice configuration is circular, its diameter can be liberally selected. For example, the range of 0.5–5 mm$\phi$ can be adopted.

The mixing ratio of the wax and active ingredient is dependent on the extruder type and ratings, screw geometry, wax and active ingredient used, and additives employed but is generally within the range of 1:99 through 999:1 and preferably 5:95–99:1 (wax: active ingredient). If the proportion of the wax is less than 1 part to 99 parts of the active ingredient, no satisfactory wax matrix can be obtained and, moreover, the shearing and kneading load within the barrel structure tends to become large. On the other hand, if the proportion of the wax is larger than 99 parts to 1 part of the active ingredient, formation of a wax matrix and processing within the barrel structure are not adversely affected but the final dosage form, for instance, will become too bulky for oral intake.

The barrel and die temperatures are selected according to extruder type and ratings, screw geometry, types of wax and active ingredient, and additives used, among other factors. Generally speaking, these temperatures can be set at levels lower than the melting point of the wax by about 5°–30° C., preferably about 10°–20° C. If the temperatures are higher than the above-mentioned levels, the wax emerging from the die will be in molten state so that an extrudate of desired shape may not be obtained. Moreover, the pulverizing process and other operations may become complicated and even the content uniformity be adversely affected. However, the temperatures of the upstream and/or intermediate barrel (in the case of an extruder having 5 barrels, the 2nd and 3rd barrels from the inlet side) may be set to a level not below the melting point of the wax so as to melt the wax and the subsequent barrels (in the case of the above extruder having 5 barrels, the 4th and 5th barrels from the inlet side) and the die can be set at a level below said melting point. Even in such cases, the wax matrix of this invention can still be obtained. There also are cases in which the wax matrix of this invention can be obtained even using still lower temperature settings and such cases also fall within the scope of this invention. However, it is often necessary to use some ingeniety such as adding purified water or a plasticizer, for instance, in the course of processing.

The wax that can be used in the method of this invention includes waxes of the animal or vegetable origin, synthetic waxes and semi-synthetic waxes. Specifically, waxes which are solid at room temperature such as higher fatty acids, higher fatty acid ester derivatives, higher alcohols and higher alcohol ester derivatives, among others, can be mentioned. To be more specific, the following typical examples may be cited.

1. Higher fatty acids:

Lauric acid, tridecanoic acid, myristic acid, pentadecanoic acid, palmitic acid, margaric acid, stearic acid, nonadecanoic acid, arachidonic acid, behenic acid, lignoceric acid, cerotic acid, montanic acid.

2. Higher fatty acid ester derivatives:

The glyceryl, ethylene glycol, propylene glycol, sorbitol, polyethylene glycol and other esters of the fatty acids listed under (1). Saturated fatty acid glycerides derived from animals or vegetable, mixtures thereof, and hydrogenated oils available from said glycerides of the animal or vegitable origin. Glycerides of oleic acid, linolic acid, linolenic acid, ricinoleic acid, etc. and mixtures thereof.

3. Higher alcohols:

Pentadecanol, hexadecanol, heptadecanol, octadecanol, nonadecanol, eicosanol, wool alcohol, cholesterol.

4. Higher alcohol ester derivatives:

Cholesteryl palmitate and phytosterol palmitate.

The above-mentioned waxes can be used singly but two or more species can likewise be used. Even when two or more species are employed, the wax matrix of this invention can still be obtained.

The active ingredient that can be used is not particularly restricted unless it is decomposed by the wax used. Specifically the following drugs can be mentioned.

1. Antipyretic/analgesic/antiinflammatory agents:

Indomethacin, aspirin, diclofenac sodium, ketoprofen, ibuprofen, mefenamic acid, dexamethasone, dexamethasone sulfate sodium, hydrocortisone, prednisolone, azulene, phenacetin, isopropylantipyrin e, acetaminophen, benzydamine hydrochloride, phenylbutazone, flufenamic acid, mephenamic acid, sodium salicylate, choline salicylate, sasapyrine, clofezone, etodolac.

2. Antiuler drugs:

Sulpiride, cetraxate hydrochloride, gefarnate, irsogladine maleate, cimetidine, unitidine hydrochloride, femotidine, nistidine, roxatidine acetate hydrochloride.

3. Coronary vasodilators:

Nifedipine, isosorbide dinitrate, diltiazem hydrochloride, trapidil, dipyridamole, dilazep dihydrochloride, methyl 2,6-dimethyl-4-(2-nitrophenyl)-5-(2-oxo-1,3,2-dioxaphosphorinan-2-yl)-1,4-dihydropyridine-3-carboxylate, verapamil, nicardipine, nicardipine hydrochloride, verapamil hydrochloride.

4. Peripheral vasodilators:

Ifenprodil tartrate, cinepazide maleate, cyclandelate, cinnarizine, pentoxifylline.

5. Antibiotics:

Ampicillin, amoxicillin, cefalexin, erythromycin ethylsuccinate, bacampicillin hydrochloride, minocycline hydrochloride, chloramphenicol, tetracyline, erythromycin.

6. Synthetic antimicrobial agents:

Nalidixic acid, piromidic acid, pipemidic acid trihydrate, enoxacin, cinoxacin, ofloxacin, norfloxacin, ciprofloxacin hydrochloride, sulfameth oxazole.rimethoprim, 6-fluoro-1-methyl-7-[4-(5-methyl-2-oxo-1,3-dioxolen-4-yl)methyl-1-piperazinyl]-4-oxo-4H[1,3]thiazeto[3,2-a]quinoline-3-carboxylic acid.

7. Anticonvulsants:

Propantheline bromide, atropine sulfate, oxobium bromide, timepidium bromide, butylscopolamine bromide, trospium chloride, butropium bromide, N-methylscopolamine methylsulfate, octatropine methylbromide, butropium bromide.

8. Antitussive/antiasthmatic agents:

Theophylline, aminophylline, methylephedrine hydrochloride, procaterol hydrochloride, trimetoquinol hydrochloride, codeine phosphate, sodium cromoglycate, tranilast, dextromethorphan hydrobromide, dimemorfan phosphate, clobutinol hydrochloride, fominoben hydrochloride, benproperine phosphate, tipepidine hibenzate, eprazinone hydrochloride, clofedanol hydrochloride, ephedrine hydrochloride, noscapine, carbetapentane citrate, oxeladin tannate, isoaminile citrate, eprazinone hydrochloride.

9. Bronchodilators:

Diprophylline, salbutamol sulfate, clorprenaline hydrochloride, formoterol fumarate, orciprenaline sulfate, pirbuterol hydrochloride, hexoprenaline sulfate, bitolterol mesilate, clenbuterol hydrochloride, terbutaline sulfate, mabuterol hydrochloride, fenoterol hydrobromide, methoxyphenamine hydrochloride.

10. Diuretics:

Furosemide, acetazolamide, trichlormethiazide, methyclothiazide, hydrochlorothiazide, hydroflumethiazide, ethiazide, cyclopenthiazide, spironolactone, triamterene, chlorothiazide, piretanide, mefruside, etacrynic acid, azosemide, clofenamide.

11. Muscle relaxants:

Chlorphenesin carbamate, tolperisone hydrochloride, eperisone hydrdchloride, tizanidine hydrochloride, mephenesin, chlorzoxazone, phenprobamate, methocarbamol, chlormezanone, pridinol mesylate, afloqualone, baclofen, pridinol mesylate, dantrolene sodium.

12. Cerebral metabolism improving agents:

Meclofenoxate hydrochloride.

13. Minor tranquilizers:

Oxazolam, diazepam, clotiazepam, medazepam, temazepam, fludiazepam, meprobamate, nitrazepam, chlordiazepoxide.

14. Major tranquilizers:

Sulpiride, clocapramine dihydrochloride, zotepine, chlorpromazine, haloperidol.

15. β-Blockers:

Pindolol, propranolol hydrochloride, carteolol hydrochloride, metoprolol tartrate, labetalol hydrochloride, oxaurenol hydrochloride, acebutolol hydrochloride, bufetolol hydrochloride, alprenolol hydrochloride, arotinolol hydrochloride, oxprenolol hydrochloride, nadolol, bucumolol hydrochloride, indenonol hydrochloride, timolol maleate, befunolol hydrochloride, bupranolol hydrochloride.

16. Antiarrythmic drugs:

Procainamide hydrochloride, disopyramide, ajmaline, quinidine sulfate, aprindine hydrochloride, propafenone hydrochloride, mexiletine hydrochloride.

17. Arthrifuges:

Allopurinol, probenecid, colchicine, sulfinpyrazone, benzbromarone, bucolome.

18. Anticoagulants:

Ticlopidine hydrochloride, dicumarol, warfarin potassium.

19. Antiepileptics:

Phenytoin, sodium valproate, metharbital, carbamazepine.

20. Antihistaminics:

Chlorpheniramine maleate, clemastine fumarate, mequitazine, alimemazine tartrate, cycloheptazine hydrochloride.

21. Antiemetics:

Difenidol hydrochloride, metoclopramide, domperidone, betahistine mesylate, trimebutine maleate.

22. Antihypertensive agents:

Dimethylaminoethyl reserpilinate dihydrochloride, rescinnamine, methyldopa, prazosin hydrochloride, bunazosin hydrochloride, clonidine hydrochloride, budralazine, urapidil.

23. Sympathomimetic drugs:

Dihydroergotamine mesylate, isoproterenol hydrochloride, etilefrine hydrochloride.

24. Expectorants:

Bromhexine hydrochloride, carbocisteine, cisteine ethyl ester hydrochloride, cisteine methyl ester hydrochloride.

25. Oral antidiabetics:

Glibenclamide, tolbutamide, glymidine sodium.

26. Cardiovascular drugs:

Ubidecarenone, ATP-2Na.

27. Iron preparations:

Ferrous sulfate, anhydrous iron sulfate.

28. Vitamins:

Vitamin $B_1$, vitamin $B_2$, vitamin $B_6$, vitamin $B_{12}$, vitamin C, folic acid.

29. Therapeutic drugs for pollakiurea:

Flavoxate hydrochloride, oxybutynin hydrochloride, terodiline hydrochloride, 4-diethylamino-1,1-dimethyl-2-butinyl(±)-α-cyclohexyl-α-phenylglycolate hydrochloride monohydrate.

30. Angiotensin converting enzyme inhibitors:

Enalapril maleate, alacepril, delapril hydrochloride.

In the method of this invention, various additives such as release-modulating agents, plasticizers, etc. can be included in formulations. Such additives can be used in a proportion of 5–90% (w/w), preferably 5–70% (w/w), relative to the wax. While these additives can be added in the stage of mixing the wax with the active ingredient, they can be fed into the barrel structure of the extruder through an auxiliary feeding port with which the extruder is generally provided.

The additives that can be used in the method of this invention are dellulose derivatives, starch and starch derivatives, sugars, and inorganic substances. Specifically the following substances can be mentioned.

1. Cellulose derivatives:

Crystalline cellulose, crystalline cellulose carboxymethylcellulo se sodium, methylcellulose, ethyl cellulose, hydroxypropylcellulose, low substituted hydroxypropylcellulose, hydroxypropylmethylcellulose 2208, hydroxypropylmethylcellulose 2906, hydroxypropylmethylcellulose 2910, hydroxypropylmethylcellulose acetate succinate, carboxymethylcel lulose, carboxymethylcellulose calcium, croscarmellose sodium.

2. Starch and its derivatives:

Wheat starch, corn starch, potato starch, dextrin, pregelatinized starch, partly pregelatinized starch, carboxymethylstarch sodium, pullulan.

3. Sugars and sugar alcohols:

Sucrose, mannitol, xylitol, sorbitol.

4. Inorganic substances:

Kaolin, talc, magnesium stearate, titanium dioxide, precipitated calcium carbonate, calcium hydrogen phosphate.

5. Plasticizers:

Triethyl citrate, triacetin, medium-chain fatty acid triglycerides, propylene glycol.

In the method of this invention, the load processed in the barrel structure is extruded as a wax matrix continuously from the orifices of the die and this extrudate can be cut to length with a rotary cutter that can be mounted on the forword end of the die. By this operation, granules or pellets can be directly obtained without resort to specific size selection. Moreover, when the wax matrix granules thus obtained have edges, these edges can be removed by feeding the wax matrix granules continuously into a rounding device such as Marumerizer Q-230 [Fiji Powder Co., Ltd.] or CF-360S centrifugal fluidized coating granulator [Freund Industrial Co., Ltd.]. In this manner, a burst of release in the early phase of dissolution can be successfully controlled.

EFFECTS OF THE INVENTION (1) In accordance with this invention, a wax matrix of improved drug content uniformity can be produced on a high production scale in a reduced time and in higher yield by means of an equipment (extruder) which is smaller than the equipment used in the prior art technology. This effect may be attributed to the fact that the extruder is a continuous processing machine.

(2) In accordance with this invention, a wax matrix with a desired shape can be obtained. This is because, in the case of an extruder, its die orifice configuration and size can be freely selected according to the objective. Therefore, small-diameter cylinders or flakes, for instance, of a wax matrix which connot be obtained by the prior art technology can be success fully obtained.

(3) In accordance with this invention, a wax matrix can be produced at a temperature below the melting point of the wax. Therefore, this invention is especially useful for providing a wax matrix containing a heat-labile active ingredient.

(4) Since an extruder has a self-cleaning mechanism, the interior of the extruder barrel structure is not easily soiled and the cleaning operation is simplified as compared with the equipment used in the prior art technology. Therefore, the invention does not require a chlorine-containing cleaning solvent or, if it does, requires only a minimal quantity so that problems associated with waste water disposal etc. can be minimized.

(5) The above facts suggest that the method of this invention is advantageous for commercial-scale production.

BEST MODE FOR CARRYING OUT THE INVENTION

The following examples and test examples are intended to illustrate this invention in further detail.

It should be understood that the numbers assigned to the respective barrels are in the order starting with the barrel closest to the feeding side (inlet side).

EXAMPLE 1

One-hundred (100) grams of Compound A (6-fluoro-1-methyl-7-[4-(5-methyl-2-oxo-1,3-dioxolen-4-yl)methyl-1-piperazinyl]-4-oxo-4H-[1,3]thiazeto[3,2-a]quinoline-3-carboxylic acid; mean particle diameter 135 µm; the same applies hereinafter) was mixed with 50 g of hydrogenated castor oil (trade name; Castor Wax A, NIPPON OIL & FATS Co., Ltd. (NOF); the same applies hereinafter) and the resulting mixed powder was fed to the hopper of a twin-screw extruder (KEXN-30S-20; Kurimoto, Ltd.; the same applies hereinafter) equipped with a die with an orifice diameter of 1 mm$\phi$×5 at a rate of 35 g per minute and, using the temperature settings of barrel 1=25° C., barrels 2, 3, 4 and 5=80° C., and die=80° C., extruded at an extrusion speed of 80 rpm to provide an extrudate (wax matrix).

EXAMPLE 2

One-hundred (100) grams of Compound A was mixed with 100 g of hydrogenated castor oil and the resulting mixture was fed to the hopper of a twin-screw extruder equipped with a die having 1 mm$\phi$×5 orifices at a rate of 35 g/minute and, using the temperature settings of barrel 1=25° C., barrels 2, 3, 4 and 5=80° C., and die=80° C., extruded at an extrusion speed of 80 rpm to provide an extrudate (wax matrix).

EXAMPLE 3

One-hundred (100) grams of Compound A was mixed with 200 g of hydrogenated castor oil and the resulting mixed powder was fed to the hopper of a twin-screw extruder equipped with a die having 1 mm$\phi$×5 orifices at a rate of 35 g/minute and using the temperature settings of barrel 1=25° C., barrels 2, 3, 4 and 5=80° C., and die=80° C., extruded at an extrusion rate of 80 rpm to provide an extrudate (wax matrix).

EXAMPLE 4

Three-hundred (300) grams of Compound A was mixed with 600 g of stearic acid (trade name: Powdery Stearic Acid, manufactured by NOF; the same applies hereinafter) and the resulting mixed powder was fed to the hopper of a twin-screw extruder equipped with a die having 1 mm$\phi$×5 orifices at a rate of 50 g/min. and using the temperature settings of barrel 1=25° C., barrels 2, 3, 4 and 5=45° C., and die=45° C., extruded at an extrusion speed of 80 rpm to provide an extrudate (wax matrix).

EXAMPLE 5

Fifty (50) grams of indomethacin bulc powder (mean particle diameter 74 µm) was mixed with 200 g of stearic acid and 100 g of Macrogol 6000 (trade name: Macrogal 6000 Powder, manufactured by Sanyo Chemicals Industries, Ltd.; the same applies hereinafter) and the resulting mixed powder was fed to the hopper of a twin-screw extruder equipped with a die having 2 mm$\phi$×3 orifices at a feeding rate of 40 g per minute and using the temperature settings of barrel 1=25° C., barrels 2, 3, 4 and 5=48° C., and die=45° C., extruded at an extrusion speed of 100 rpm to provide an extrudate (wax matrix).

EXAMPLE 6

Fifty (50) grams of indomethacin bulc powder (mean particle diameter 74 µm) was mixed with 150 g of stearic acid and 150 g of Macrogol 6000. The resulting mixed powder was fed to the hopper of a twin-screw extruder equipped with a die having 2 mm$\phi$×3 orifices at a feeding rate of 40 g per minute and using the temperature settings of barrel 1=25° C., barrels 2, 3, 4 and 5=48° C., and die=45° C., extruded at an extrusion speed of 100 rpm to provide an extrudate (wax matrix).

EXAMPLE 7

Fifty (50) grams of indomethacin bulc powder (mean particle diameter 74 µm) was mixed with 100 g of stearic acid and 200 g of Macrogol 6000 and the resulting mixed powder was fed to the hopper of a twin-screw extruder equipped with a die having 2 mm$\phi$×3 orifices at a rate of 40 g per minute and, using the temperature settings of barrel 1=25° C., barrels 2, 3, 4 and 5=48° C., and die=45° C., extruded at an extrusion speed of 100 rpm to provide an extrudate (wax matrix).

EXAMPLE 8

Fifty (50) grams of dehydrocholic acid powder (mean particle diameter 78 µm) was mixed with 300 g of wheat flour (trade name: Violet, manufactured by Nissin Flour Milling Co., Ltd.) and 150 g of stearic acid. The resulting mixed powder was fed to the hopper of a twin-screw extruder equipped with a die having 1 mm$\phi$×5 orifices at a feeding rate of 40 g per minute and using the temperature settings of barrel 1=25° C., barrel 2=80° C., barrels 3, 4 and 5=100° C., and die=100° C., extruded at an extrusion speed of 100 rpm while purified water was poured from the top of barrel 3 at a rate of 10 ml/min to provide an extrudate.

EXAMPLE 9

Two-hundred (200) grams of acetaminophen bulc powder (mean particle diameter 40 µm) was mixed with 100 g of hydrogenated castor oil and the resulting mixture was fed to the hopper of a twin-screw extruder equipped with a die having 1 mm$\phi$×5 orifices at a rate of 40 g per minute and, using the temperature settings of barrel 1=25° C., barrels 2, 3, 4 and 5=80° C., and die=80° C., extruded at an extrusion speed of 50 rpm to provide an extrudate (wax matrix).

EXAMPLE 10

One-hundred-fifty (150) grams of acetaminophen bulc powder (mean particle diameter 40 µm) was mixed with 150 g of hydrogenated castor oil and the resulting mixture was fed to the hopper of a twin-screw extruder equipped with a die having 1 mm$\phi$×5 orifices at a rate of 40 g per minute and, using at the temperature settings of barrel 1=25° C., barrels 2, 3, 4 and 5=80° C., and die=80° C., extruded at an extrusion speed of 50 rpm to provide an extrudate (wax matrix).

EXAMPLE 11

One-hundred (100) grams of acetaminophen bulc powder (mean particle diameter 40 µm) was mixed with 200 g of hydrogenated castor oil and the resulting mixture was fed to the hopper of a twin-screw extruder equipped with a die having 1 mm$\phi$×5 orifices at a rate of 40 g per minute and, using the temperature settings of barrel 1=25° C., barrels 2, 3, 4 and 5=80° C., and die=80° C., extruded at an extrusion speed of 50 rpm to provide an extrudate (wax matrix).

EXAMPLE 12

One-hundred (100) grams of acetamininophen bulc powder (mean particle diameter 40 µm) was mixed with 300 g of hydrogenated castor oil and the mixture was fed to the hopper of a twin-screw extruder equipped with a die having 1 mm$\phi$×5 orifices at a rate of 40 g per minute and using the temperature settings of barrel 1=25° C., barrels 2, 3, 4 and 5=80° C., and die=80° C., extruded at an extrusion speed of 50 rpm to provide an extrudate (wax matrix).

Comparison Example 1

Forty (40) grams of Compound A was mixed with 80 g of stearic acid and the mixture was put in a stainless steel beaker (diameter 9.5 cm, height 15 cm) and melted by heating on a water bath at 70° C. After thorough dispersing, the beaker was taken out from the water bath and allowed to stand at 25° C. for spontaneous cooling and coagulation to provide a content uniformity comparison test sample.

Test Example 1

The extrudates obtained in Examples 1, 2 and 3 were respectively comminuted by means of a roll granulator (GRN-1041; manufactured by Nippon Granulator; the same applies hereinafter) and the powder fraction within the range of No. 16 (1000 µm) to No. 30 (500 µm) sieves was taken as a dissolution test sample. From each of these fractions, the equivalent of 100 mg of Compound A was weighed out and put in 900 ml of the first fluid (pH 1.2) according to Japanese Pharmacopoeia Dissolution Test, and the dissolution test was performed by the paddle method (paddle speed: 100 rpm) using a measuring wavelength of 355 nm.

As shown in FIG. 1, the extrudates obtained by the method of this invention were delayed in release of the active ingredient in proportion with the amount of hydrogenated castor oil. On the other hand, the powdery mixtures prior to extruder processing showed rapid release.

The above results indicate that the method of this invention provided a slow-release wax matrix.

Test Example 2

The extrudates obtained in Examples 5, 6 and 7 were respectively comminuted by means of a roll granulator and the powder fraction within the range of No. 16 (1000 µm) to No. 30 (500 µm) sieves was taken as a dissolution test smaple. From each of these fraction samples, the equivalent of 20 mg of indomethacin was taken and poured in 900 ml of purified water and the dissolution test was performed by the paddle method (paddle speed 100 rpm) using a measuring wavelength of 320 nm.

As shown in FIG. 2, the extrudates obtained by the method of this invention showed increases in the rate of release of the active ingredient in proportion with the amount of macrogol. The powdery mixture prior to extruder processing showed rapid release.

The above results indicate that the method of this invention provided a controlled-release wax matrix.

Test Example 3

The extrudate obtained in Example 8 was fed to an electric air-current dryer set to 50°±3° C. and dried for about 5 hours. It was then comminuted by means of a roll granulator and the powder fraction within the range of No. 16 (1000 µm) to No. 30 (500 µm) sieves was used as a sample for dissolution and sensory tests. A 500 mg portion of the sample was put in 900 ml of purified water and the dissolution test was performed by the paddle method (paddle speed 100 rpm) using a measuring wavelength of 289 nm.

As shown in FIG. 3, dehydrocholic acid was substantially not released for a while. On the other hand, the mixed powder prior to extruder processing showed a rapid release of dehydrocholic acid upon pouring in water.

The above results show conclusively that the method of this invention provided a controlled-release wax materix.

Test Example 4

The extrudates obtained in Examples 9, 10, 11 and 12 were respectively comminuted by means of a roll granulator and, in each case, the powder fraction within the range of No. 16 (1000 µm) to No. 30 (500 µm) sieves was taken as a dissolution test sample. From each of these samples, the equivalent of 25 mg of acetaminophen has weighed out and put in 900 ml of purified water and the dissolution test was performed by the paddle method (paddle speed 100 rpm) using a measuring wavelength of 244 nm.

As shown in FIG. 4, the extrudates obtained by the method of this invention showed a retardation of release which was proportional to the amount of hydrogenated castor oil.

The above results indicate clearly that the method of this invention provided a controlled-release wax matrix.

Test Example 5 (Content uniformity test)

The extrudate according to Example 4 was serially sampled to provide an early sample (up to 300 g of processed powdery mixture), an intermediate sample (300–600 g of processed powdery mixture), and a late sample (600 to 900 g of processed powdery mixture). Each of these samples was comminuted by means of a roll granulator and, in each case, the powder fraction in the range of No. 16 (1000 µm) to No. 30 (500 µm) sieves was taken as a content uniformity test sample.

From each sample, about 60 mg was weighed out and dissolved in N,N-dimethylformamide (adjusted to 100 ml)

and Compound A was assayed by high performance liquid chromatography (HPLC). From the solidified sample obtained in Comparison Example 1, too, 50 mg (approx.) samples were taken from 5 positions each of the top and bottom surfaces and the assay of Compound A was performed in the same manner as above. The results are shown in Tables 1 and 2.

The HPLC assay conditions were; detection by ultraviolet spectrophotometer (exciting wavelength 275 nm), column: Inertsil ODS-2 (4.6×250 mm), column temperature: 40° C., mobile phase: sodium octane sulfonate-containing phosphoric acid-acetonitrile, flow rate: adjusted (in each test) so that the retention time of Compound A would be 6 minutes.

TABLE 1

| Percentage (%) of active ingredient in the extrudate obtained in Example 4 (n = 5) | | |
|---|---|---|
| Early | Intermediate | Late |
| 100 ± 1.3 | 99.9 ± 1.8 | 100.6 ± 1.7 |

Mean ± standard deviation ($\sigma_{n-1}$)

TABLE 2

| Percentage (%) of active ingredient in the solidified sample obtained in Comparison Example 1 (n = 3) | | | | |
|---|---|---|---|---|
| 1 | 2 | 3 | 4 | 5 |
| Top side | | | | |
| 76.3 ± 12.3 | 71.9 ± 23.7 | 70.9 ± 18.4 | 85.2 ± 5.9 | 55.9 ± 5.0 |
| Bottom side | | | | |
| 157.8 ± 18.4 | 172.3 ± 10.0 | 185.1 ± 18.0 | 178.3 ± 32.4 | 95.2 ± 23.7 |

Mean ± standard deviation ($\sigma_{n-1}$)

It is apparent from Tables 1 and 2 that compared with the wax matrix obtained in Comparison Example 1, the wax matrix produced by the method of this invention was very satisfactory in content uniformity.

Test Example 6 (Sensory Test data)

For the assessment of bitterness of the extrudate obtained in Example 8, a functional test was carried out using 10 adult male panelists. The test procedure was as follows. Each panelist was instructed to put the mixed powder prior to extruder processing and the size-selected granular extrudate in the mouth and rated the bitterness of each sample according to the following evaluation criteria.

| Very bitter | ±3 |
|---|---|
| Bitter | ±2 |
| Slightly bitter | ±1 |
| Bitterness masked-not bitter | ±0 |

TABLE 3

| Results | |
|---|---|
| Mixed powder | 2.8 ± 0.4 |
| Granules of the invention | 0.3 ± 0.5 |

Significant difference at 99% confidence limit

It is apparent from Table 3 that the wax matrix obtained by the method of this invention does not substantially give a bitter sensation, indicating that the bitterness had been successfully masked.

Figure 1:
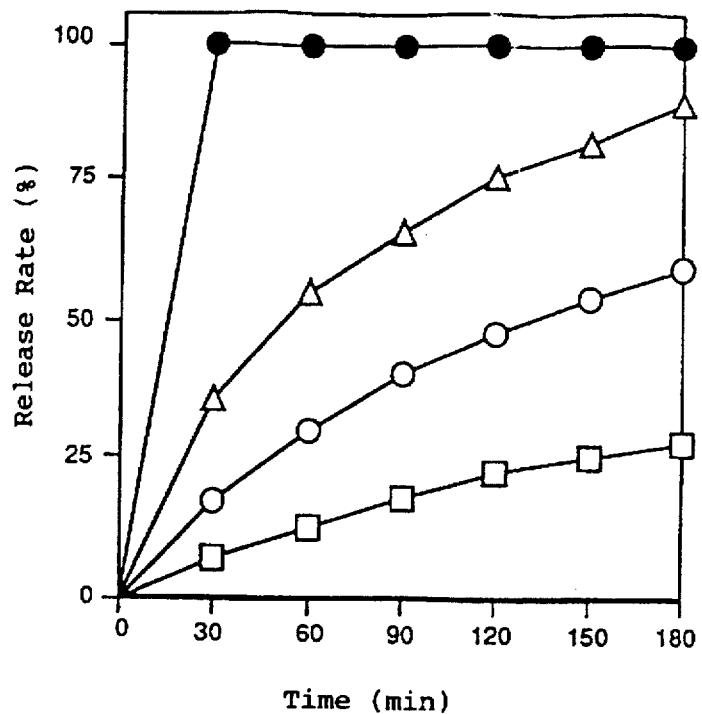
FIG. 1 shows the results of a dissolution test. The abscissa represents time (minutes) and the ordinate represents release rate (%). -□- represents the release curve of the extrudate (wax matrix) obtained in Example 1, -O- represents the release curve of the extrudate (wax matrix) obtained in Example 2, -Δ- represents the release curve of the extrudate (wax matrix) obtained in Example 3, and -●- represents the release curve of the mixed powder obtained by blending 100 g of Compound A with 200 g of hydrogenated castor oil (corresponding to the mixing ratio of the extrudate of Example 3).
Figure 2:
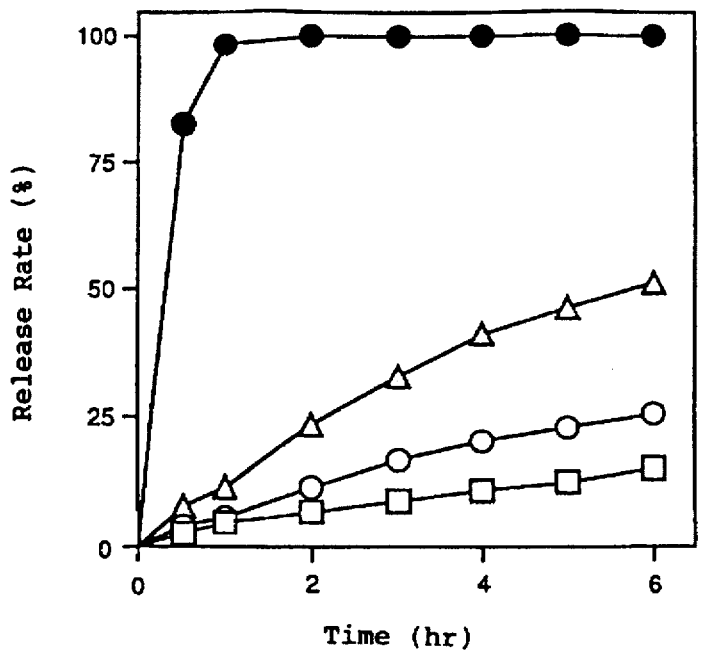
FIG. 2 shows the results of a dissolution test. The abscissa represents time (hours) and the ordinate represents release rate (%). -□- represents the release curve of the extrudate (wax materix) obtained in Example 5, -O- represents the release curve of the extrudate (wax matrix) obtained in Example 6, -Δ- represents the release curve of the extrudate (wax matrix) obtained in Example 7, and -●- represents the release curve of the mixed powder obtained by mere blending of 50 g of indomethacin, 200 g of stearic acid and 100 g of macrogol 6000 (corresponding to the mixing ratio of the extrudate of Example 5).
Figure 3:
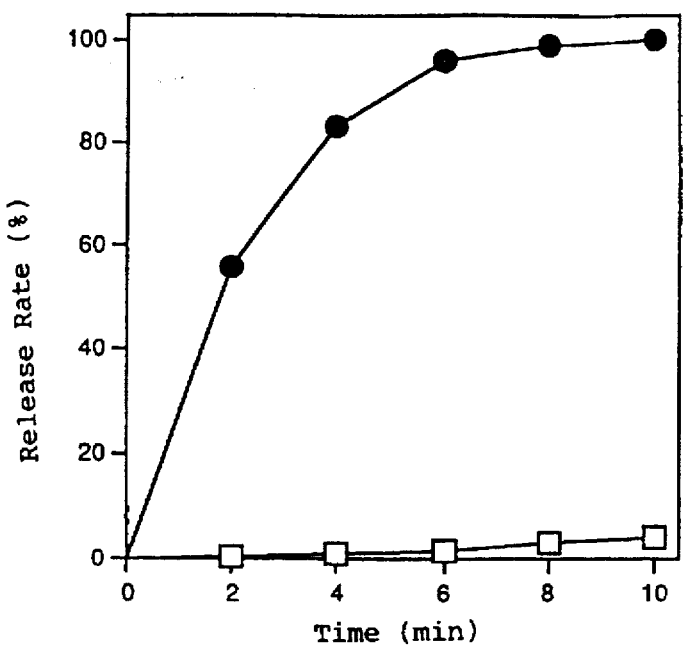
FIG. 3 shows the results of a dissolution test. The abscissa represents time (minutes) and the ordinate represents release rate (%). -□- represents the release curve of the extrudate (wax materix) obtained in Example 8, and -●- represents the release curve of the mixed powder obtained by mere blending of 50 g of dehydrocholic acid, 300 g of wheat flour and 150 g of stearic acid (corresponding to the mixing ratio of the extrudate of Example 5).
Figure 4:
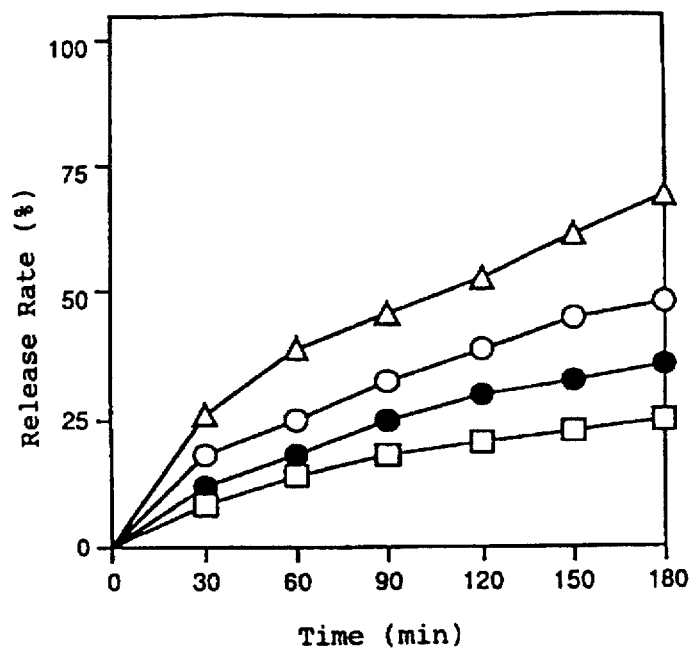
FIG. 4 shows the results of a dissolution test. The abscissa represents time (minutes) and the ordinate represents release rate (%). -Δ- represents the release curve of the extrudate (max matrix) obtained in Example 9, -O- represents the release curve of the extrudate (wax matrix) obtained in Example 10, -●- represents the release curve of the extrudate (wax matrix) obtained in Example 11, and -□- represents the release curve of the extrudate (wax matrix) obtained in Example 12.

We claim:

1. A method of producing a wax matrix for controlling release of a pharmaceutically active material contained therein, said method comprising the steps of feeding a wax and the pharmaceutically active ingredient into a multi-screw extruder and thoroughly mixing the wax with the pharmaceutically active material using the multi-screw extruder, which is maintained at a temperature below the melting point of the wax during the mixing, to form a wax matrix, wherein the wax matrix thus produced provides a controlled release of the active ingredient.

2. The method of claim 1, wherein the multi screw extruder comprises a twin screw compounding extruder equipped with kneading paddle means on screw shafts of said extruder, whereby said wax and active ingredient pass said kneading paddle means and are sheared and kneaded together thereby.

3. The method of claim 2, wherein said wax has a melting point at a specific temperature and wherein said production of the wax matrix is effected at a temperature below said melting point.

4. The method of claim 2, wherein the specific temperature at which said wax melts, is at or above a temperature at which the pharmaceutically active ingredient is degraded thereby and wherein the temperature at which the wax matrix is effected is below the degradation temperature of the active ingredient.

5. The method of claim 2, wherein the ratio of said wax to said active ingredient ranges from 1:99 to 99:1 by weight.

6. The method of claim 2, wherein said method is a continuous process and wherein said multi-screw extruder comprises self cleaning means.

7. The method of claim 1, wherein said wax is hydrogenated castor oil and said pharmaceutically active ingredient is selected from the group consisting of Compound A, and acetominophen.

8. The method of claim 1, wherein said wax is stearic acid and said pharmaceutically active ingredient is selected from the group consisting of 6-fluoro-1-methyl-7-[4-(5-methyl-2-oxo-1,3-dioxolen-4-yl)methyl-1-piperazinyl]-4-oxo-4H-[1,3]thiazeto[3,2-a]quinoline-3 -carboxylic acid indomethacin, dehydrocholic acid with wheat flour, and acetominophen.

9. The method of claim 1, wherein said wax matrix is extruded through a die and cut to form pellets or granules of desired size by a continuously operating rotary cutter.

10. The method of claim 9, wherein edges of the pellets or granules are removed by continuously being fed into contact with rounding device means.

11. A method for reducing the bitterness of a pharmaceutically active ingredient comprising the steps of including said ingredient in a wax matrix in accordance with the method of claim 2.

12. The method of claim 1, wherein the wax is a higher fatty acid or its ester derivative, wherein the higher fatty acid is selected from the group consisting of lauric acid, tridecanoic acid, myristic acid, pentadecanoic acid, palmitic acid, margaric acid, stearic acid, nonadecanoic acid, arachidonic acid, behenic acid, lignoceric acid, cerotic acid, and montanic acid.

13. The method of claim 1, wherein the wax is selected from the group consisting of saturated fatty acid glycerides of vegetable origin, saturated fatty acid glycerides of animal origin, hydrogenated oils from saturated fatty acid glycerides of the vegetable origin, hydrogenated oils from saturated fatty acid glycerides of the animal origin, pentadecanol, hexadecanol, heptadecanol, octadecanol, nonadecanol, eicosanol, wool alcohol, cholesterol, cholesteryl palmitate and phytosterol palmitate.

14. The method of claim 1, wherein the pharmaceutically active ingredient is selected from the group consisting of an antipyretic/analgesic/antiinflammatory agent, antiulcer agent, coronary vasodilator, peripheral vasodilator, antibiotic, synthetic antimicrobial agent, anticonvulsant, antitussive/antiasthmatic agent, bronchodilator, diuretic, muscle relaxant, cerebral metabolism improving agent, tranquilizer, β-blocker, antiarrhythmic drug, arthrifuge, anticoagulant, antiepileptic agent, antihistaminic agent, antihypertensive agent, sympathomimetic drug, expectorant, oral antidiabetic drug, cardiovascular drug, iron preparation, vitamin, drug for pollakiurea and angiotensin converting enzyme inhibitor.

15. The method of claim 14, wherein the antipyretic/analgesic/antiinflammatory agent is selected from the group consisting of indomethacin, aspirin, diclofenac sodium, ketoprofen, ibuprofen, mefenamic acid, dexamethasone, dexamethasone sulfate sodium, hydrocortisone, prednisolone, azulene, phenacetin, isopropylantipyrine, acetaminophen, benzydamine hydrochloride, phenylbutazone, flufenamic acid, mephenamic acid, sodium salicylate, choline salicylate, sasapyrine, clofezone and etodolac, the antiulcer agent is selected from the group consisting of sulpiride, cetraxate hydrochloride, gefarnate, irsogladine maleate, cimetidine, unitidine hydrochloride, femotidine, nistidine and roxatidine acetate hydrochloride, the coronary vasodilator is selected from the group consisting of nifedipine, isosorbide dinitrate, diltiazem hydrochloride, trapidil, dipyridamole, dilazep dihydrochloride, methyl 2,6-dimethyl-4-(2-nitrophenyl)-5-(2-oxo-1,3,2-dioxaphosphorinan-2-yl)-1,4-dihydropyridine-3-carboxylate, verapamil, nicardipine, nicardipine hydrochloride and verapamil hydrochloride, the peripheral vasodilator is selected from the group consisting of ifenprodil tartrate, cinepazide maleate, cyclandelate, cinnarizine and pentoxifylline, the antibiotic is selected from the group consisting of ampicillin, amoxicillin, cefalexin, erythromycin ethylsuccinate, bacampicillin hydrochloride, minocycline hydrochloride, chloramphenicol, tetracycline and erythromycin, the synthetic antimicrobial agent is selected from the group consisting of nalidixic acid, piromidic acid, pipemidic acid trihydrate, enoxacin, cinoxacin, ofloxacin, norfloxacin, ciprofloxacin hydrochloride, sulfameth oxazole trimethoprim and 6-fluor-1-methyl-7-[4-(5-methyl-2-oxo-1,3-dioxolen-4-yl)methyl-1-peperazinyl]-4-oxo-4H[1,3]thiazeto[3,2-a]quinoline-3-carboxylic acid, the anticonvulsant is selected from the group consisting of propantheline bromide, atropine sulfate, oxobium bromide, timepidium bromide, butylscopolamine bromide, trospium chloride, butropium bromide, N-methylscopolamine methylsulfate, octatropine methylbromide and butropium bromide, the antitussive/antiasthmatic agent is selected from the group consisting of theophylline, aminophylline, methylephedrine hydrochloride, procaterol hydrochloride, trimetoquinol hydrochloride, codeine phosphate, sodium cromoglycate, tranilast, dextromethorphan hydrobromide, dimemorfan phosphate, clobutinol hydrochloride, fominoben hydrochloride, benproperine phosphate, tipepidine hibenzate, eprazinone hydrochloride, clofedanol hydrochloride, ephedrine hydrochloride, noscapine, carbetapentane citrate, oxeladin tannate, isoaminile citrate and eprazinone hydrochloride, the bronchodilator is selected from the group consisting of diprophylline, salbutamol sulfate, clorprenaline hydrochloride, formoterol fumarate, orciprenaline sulfate, pirbuterol hydrochloride, hexoprenaline sulfate, bitolterol mesilate, clenbuterolhydrochloride, terbutaline sulfate, mabuterol hydrochloride, fenoterol hydrobromide and methoxyphenamine hydrochloride, the diuretic is selected from the group consisting of furosemide, acetazolamide, trichlormethiazide, methylclothiazide, hydrochlorothiazide, hydroflumethiazide, ethiazide, cyclopenthiazide, spironolactone, triamterene, chlorothiazide, piretanide, mefruside, etacrynic acid, azosemide and clofenamide, the muscle relaxant is selected from the group consisting of chlorphenesin carbamate, tolperisone hydrochloride, eperisone hydrochloride, tizanidine hydrochloride, mephenesin, chlorzoxazone, phenprobamate, methocarbamol, chlormezanone, pridinol mesylate, afloqualone, baclofen and dantrolene sodium, the cerebral metabolism improving agent is meclofenoxate hydrochloride, the tranquilizer is selected from the group consisting of oxazolam, diazepam, clotiazepam, medazepam, temazepam, fludiazepam, meprobamate, nitrazepam, clordiazepoxide, sulpiride, clocaproamine dihydrochloride, zotepine, chlorpromazine and haloperidol, the B-blocker is selected from the group consisting of pindolol, propranolol hydrochloride, carteolol hydrochloride, metoprolol tartrate, labetalol hydrochloride, oxaurenol hydrochloride, acebutolol hydrochloride, bufetolol hydrochloride, alprenolol hydrochloride, arotinolol hydrochloride, oxprenolol hydrochloride, nadolol, bucumolol hydrochloride, indenonol hydrochloride, timolol maleate, bufenolol hydrochloride and bupranolol hydrochloride, the antiarrhythmic drug is selected from the group consisting of procainamide hydrochloride, disopyramide, ajamline, guanidine sulfate, aprindine hydrochloride, propafenone hydrochloride, the arthrifuge is selected from the group consisting of allopurinol, probenecid, colchicine, sulfinpyrazone, benzbromarone and bucolome, the anticoagulant is selected from the group consisting of ticlopidine hydrochloride, dicumarol and warfarin potassium, the antiepileptic agent is selected from the group consisting of phenytoin, sodium valproate, metharbital and carbamazepine, the antihistaminic agent is selected from the group consisting of chlorpheniramine maleate, clemastine fumarate, mequitazine, alimemazine tartrate and cycloheptazine hydrochloride, the antiemetic is selected from the group consisting of difenidol hydrochloride, metoclopramide, domperidone, betahistine mesylate and trimebutine maleate, the antihypertensive agent is selected from the group consisting of dimethylaminoethyl reserpilinate dihydrochloride, rescinnamine, methyldopa, prazosin hydrochloride, bunazosin hydrochloride, clonidine hydrochloride, budralazine and urapidil, the sympathomimetic drug is selected from the group consisting of dihydroergotamine mesylate, isoproterenol hydrochloride and etilefrine hydrochloride, the expectorant is selected from the group consisting of bromhexine hydrochloride, carbocisteine, cysteine ethyl ester hydrochloride and cysteine methyl ester hydrochloride, the oral antidiabetic drug is selected from the group consisting of glibenclamide, tolbutamide and glymidine sodium, the cardiovascular drug is selected from the group consisting of ubidecarenone and ATP-2Na, the iron preparation is selected from the group consisting of ferrous sulfate and anhydrous iron sulfate, the vitamin is selected from the group consisting of vitamin $B_1$, vitamin $B_2$, vitamin $B_2$, vitamin C and folic acid, the drug for pollakiurea is selected from the group consisting of falvoxate hydrochloride, oxybutynin hydrochloride, terodiline hydrochloride and 4-diethylamino-1,1-dimethyl-2-butinyl (±)-α-cyclohexyl-α-phenylglycolate hydrochloride monohydrate and the angiotensin converting enzyme inhibitor is selected from the group consisting of enalapril maleate, alacepril and delapril hydrochloride.

\* \* \* \* \*